US012697246B2

(12) United States Patent
Schoeggler et al.

(10) Patent No.: US 12,697,246 B2
(45) Date of Patent: Aug. 4, 2026

(54) TEMPERATURE CONTROL DEVICE FOR FACE PATCHES

(71) Applicant: AUROX GmbH, Graz (AT)

(72) Inventors: Christoph Schoeggler, Graz (AT); Georg Wanka, Graz (AT); Heinrich Zaunschirm, Graz (AT)

(73) Assignee: AUROX GMBH, Graz (AT)

( * ) Notice: Subject to any disclaimer, the term of this patent is extended or adjusted under 35 U.S.C. 154(b) by 242 days.

(21) Appl. No.: 18/563,601

(22) PCT Filed: May 25, 2022

(86) PCT No.: PCT/EP2022/064184
§ 371 (c)(1),
(2) Date: Nov. 22, 2023

(87) PCT Pub. No.: WO2022/248543
PCT Pub. Date: Dec. 1, 2022

(65) Prior Publication Data
US 2024/0238115 A1 Jul. 18, 2024

(30) Foreign Application Priority Data

May 25, 2021 (AT) .............................. A 50412/2021

(51) Int. Cl.
*A61F 7/00* (2006.01)
*A61F 7/02* (2006.01)
(52) U.S. Cl.
CPC ............ *A61F 7/007* (2013.01); *A61F 7/0241* (2013.01); *A61F 2007/0003* (2013.01); *A61F*

2007/0004 (2013.01); *A61F 2007/0075* (2013.01); *A61F 2007/0298* (2013.01)

(58) Field of Classification Search
CPC ...... A61F 2007/0074; A61F 2007/0076; A61F 7/0241
See application file for complete search history.

(56) References Cited

U.S. PATENT DOCUMENTS

| | | | |
|---|---|---|---|
| 8,525,363 | B2 | 9/2013 | Rajadhyaksha et al. |
| 10,835,415 | B2 | 11/2020 | Johnson et al. |
| (Continued) | | | |

FOREIGN PATENT DOCUMENTS

| | | |
|---|---|---|
| KR | 20130098503 A | 9/2013 |
| KR | 20170050867 A | 5/2017 |
| (Continued) | | |

OTHER PUBLICATIONS

International Search Report and Written Opinion from corresponding International Application No. PCT/EP2022/064184 dated Sep. 14, 2022.

*Primary Examiner* — Kaitlyn E Smith
(74) *Attorney, Agent, or Firm* — Lando & Anastasi, LLP

(57) ABSTRACT

A temperature control device for face pads. The temperature control device comprises a Peltier element, at least one receptacle for supporting an eye pad, wherein each of the at least one receptacle is thermally coupled to a warm side or a cold side of the Peltier element, and a fixing device which is thermally decoupled from the Peltier element and which fastens the at least one receptacle to the warm side or the cold side in a form-fitting and/or force-locking manner.

11 Claims, 5 Drawing Sheets

(56)         References Cited

U.S. PATENT DOCUMENTS

2009/0312823 A1 *  12/2009  Patience ................. A61F 7/007
                                                        607/104
2012/0305231 A1 *  12/2012  Liang ................... A61F 7/0241
                                                        165/287
2013/0172829 A1     7/2013  Badawi
2017/0216088 A1 *   8/2017  Johnson ................... A61F 7/02
2018/0116866 A1     5/2018  Agnew
2018/0289533 A1    10/2018  Johnson et al.
2020/0405535 A1 *  12/2020  Stelzle ..................... F04C 2/08

FOREIGN PATENT DOCUMENTS

WO         2014119025  A1     8/2014
WO         2018122710  A1     7/2018
WO         2019175111  A1     9/2019

* cited by examiner

TEMPERATURE CONTROL DEVICE FOR FACE PATCHES

CROSS-REFERENCE TO RELATED APPLICATIONS

This application is a U.S. National Stage Application under 35 U.S.C. § 371 of International Application No. PCT/EP2022/064184, filed May 25, 2022, titled TEMPERATURE CONTROL DEVICE FOR FACE PATCHES, which claims priority to Austrian Application No. 50412/2021, filed May 25, 2021. International Application No. PCT/EP2022/064184 is incorporated by reference herein in its entirety.

TECHNICAL FIELD

The invention relates to temperature control devices for support elements, being temporarily applied to the facial and in particular to the periocular area, such as the so-called eye pads or philtrum pads,

BACKGROUND

Support elements that can be applied cutaneously and removed again in the periocular facial area, also known as "eye pads", are products used in the cosmetics industry to be applied by a user in the area under and/or around the eyes so as to achieve a cosmetic effect on the skin of the user. For reducing the formation of wrinkles in the cutaneous area between the nose, nasolabial folds and upper lip, known as the philtrum, it is possible to use support elements that can be applied cutaneously, also known as "philtrum pads". In particular, the targeted cutaneous application of heat or cold can be an effective means of treating pleated wrinkles.

In the prior art, for example, there are known, for example, eye pads containing an active ingredient that is slowly released onto the user's skin. This can, for example, stimulate blood circulation or, in the case of moisturizers, reduce the evaporation of water from the skin's surface, thereby improving moisture retention in the skin.

Furthermore, therapies for the treatment of eye diseases such as meibomian gland dysfunction (MGD)—a chronic abnormality of the meibomian glands (MG)—or other unpleasant or pathological changes in and around the eye can be positively supported by targeted heating or cooling of the periocular area.

In the prior art there are known devices that heat and/or cool the skin under the user's eyes. It is, therefore an ordinary practice to use natural agents such as cucumber slices or similar, which have a cooling effect by dissipating evaporation heat. There are however also known technical devices that are applied to the skin and cause the skin to be heated or cooled by means of electrical, chemical or biochemical components.

Examples thereof are described in the prior art documents US 301,931 A, U.S. Pat. No. 8,525,363 B1, US 2013/0172829 A1 or WO 2018/122710 A1.

Examples of temperature control devices that can be used to specifically heat or cool eye pads or philtrum pads prior to cutaneous application have been described in US 2018/0116866 A1 and US 2017/0216088 A1.

SUMMARY

One of the ideas of the present invention to provide a controlled heating or cooling of eye pads or philtrum pads.

A first aspect of the invention relates to an eye pad comprising an eye pad body having a first side for contacting a skin of a user, and a second side substantially opposite the first side. The eye pad body comprises a passage from the first side to the second side, and the eye pad comprises a negative pressure generating element disposed on the second side at one end of the passage, and preferably extending at least partially into the passage. According to the invention, the negative pressure generating element is at least partially elastic and is configured to provide a suction force in the passage through the eye pad body as a result of elastic deformation of the negative pressure generating element when the first side of the eye pad body is placed on the skin of the user.

By designing the eye pad according to the first aspect of the invention with the passage from the first side to the second side through the eye pad body and the negative pressure generating element, a secure fastening method is provided which does not require additional mechanical retaining means. This ensures a secure fastening of the eye pad under one of the user's eyes, which is easy to use and does not cause any unpleasant pressure points in the user's head area, resulting in a high level of wearing comfort. The suction effect also improves blood circulation in the area where the eye pad is attached. The eye pad of the first aspect of the invention prevents uncontrolled falling off from the skin of the user, without severely restricting the user's freedom of movement while using the eye pad. The eye pads are also easy to use and do not require temperature control devices to be coupled during use.

According to some embodiments of the eye pad according to the invention, the passage comprises a larger opening on the first side than on the second side. This increases the area on the user's skin to which the suction force is distributed. This reduces the likelihood of the suction effect damaging vessels in the user's skin. In addition, this further improves the wearing comfort of the eye pads according to the invention.

In some embodiments, the negative pressure generating element may comprise an extension protruding from the second side. This makes it easier for the user of the eye pad according to the invention to grip the negative pressure generating element.

According to some embodiments, the passage comprises a plurality of slots and/or holes substantially oriented in a passage direction. This divides the passage into several sections, wherein the suction effect is distributed over the several slots and/or holes. This distributes the force generated by the suction effect over a larger area of the skin surface.

According to some embodiments of the eye pad according to the invention, the slots and/or holes are disposed at an acute angle to each other, narrowing in the direction of the second side. This further increases the area of the user's skin that is exposed to the suction effect.

According to some alternative embodiments of the eye pad according to the invention, the negative pressure generating element extends from the second side to the first side of the eye pad body through the passage, and is designed as an at least partially elastic insert in the eye pad body which is open on one side in the direction of the first side. This results in an improved seal between the negative pressure generating element and the eye pad body, which means that the negative pressure and the resulting suction effect can be maintained over a longer period of time.

In several embodiments, the negative pressure generating element may comprise a flexible lip arranged on the first side of the eye pad body and surrounding the passage. This provides an improved seal between the passage through the eye pad body and the user's skin. In addition, the passage may comprise, for example, a narrow point between the first side and the second side of the eye pad body. As a result, the extent to which the user's skin can be sucked into the eye pad body is limited.

According to some embodiments of the eye pad according to the invention, the eye pad body is made of a metal and can advantageously be covered with a soft material such as silicone, latex and/or rubber. By manufacturing the eye pad body from metal, an increased heat capacity of the eye pad body is achieved, which means that the warming or cooling effect on the user's skin can be maintained over a longer period of time when the eye pad is heated or cooled. Covering the eye pad body with silicone, latex and/or rubber provides a soft surface that is pleasant to the touch and also thermally insulates the eye pad body. As a result, the risk of burns or frostbite occurring on the user's skin when using the eye pad is reduced.

According to a second aspect of the invention, a temperature control device for eye pads and/or philtrum pads comprises a Peltier element, at least one receptacle for supporting an eye pad or philtrum pad, each of the at least one receptacle being thermally coupled to a warm side or a cold side of the Peltier element, and a fixing device which is thermally decoupled from the Peltier element and fastens the at least one receptacle to the warm side or the cold side in a form-fitting and/or force-locking manner.

The thermal coupling between the at least one receptacle and the Peltier element can be provided, for example, by surface contact between the receptacle and the Peltier element. In addition, a heat-conducting paste can fill any cavities in the surface contact and thus support the heat transfer between the Peltier element and the receptacle.

The fixing device is produced, for example, from a glass fiber reinforced plastic. It can surround the at least one receptacle in portions and be fastened to a housing of the temperature control device by a detachable fastening means, in particular by a screw connection, a plug-in connection or the like.

According to some embodiments of the temperature control device, the at least one receptacle is shaped so as to correspond substantially in portions to a shape of the eye pad or philtrum pad. In this way, an eye pad or philtrum pad can be stably positioned in a recess adapted to it. In addition, this increases the contact area between the receptacle and the eye pad or philtrum pad, so that the heating or cooling of the eye pads or philtrum pads is accelerated by the heat transfer of the receptacle.

According to some embodiments, the temperature control device comprises two receptacles, wherein one of the receptacles is thermally coupled to the warm side and one of the receptacles is thermally coupled to the cold side of the Peltier element, and wherein in each case two eye pads can be supported by the two receptacles. This means that two eye pads can be cooled and heated at the same time. According to some embodiments, the temperature control device may comprise more than two receptacles, wherein at least one further receptacle for a philtrum pad may be provided in addition to two receptacles for eye pads.

According to some embodiments of the temperature control device, the at least one receptacle comprises a protrusion for placing an eye pad or philtrum pad on the protrusion. In this way, the eye pad or philtrum pad can be heated or cooled closer to its center of mass, allowing the eye pad or philtrum pad to reach the target temperature faster and more evenly distributed over the entire eye pad or philtrum pad.

According to some embodiments of the temperature control device, the at least one receptacle comprises a magnet for magnetically fastening an eye pad or philtrum pad to the receptacle. In particular, the magnet is provided on the protrusion of the receptacle. This means that an eye pad or philtrum pad, which comprises a magnetizable material or also a magnet, can be firmly fixed in the receptacle. This also means that the contact between the eye pad or philtrum pad and the receptacle corresponds to a predetermined quality.

According to some embodiments of the temperature control device, the at least one receptacle comprises a temperature conducting material, in particular aluminum, copper or an aluminum or copper alloy, and is produced in particular by a casting method or a forging method. In this way there is ensured sufficient thermal conductivity of the receptacle.

According to some embodiments of the temperature control device, the at least one receptacle comprises a temperature sensor and a control unit connected to the temperature sensor and the Peltier element. The control unit is configured to regulate the heating or cooling power of the Peltier element on the basis of the temperature of the at least one receptacle detected by the temperature sensor.

According to a further development of the temperature control device, the control unit is configured to regulate the heating or cooling power of the Peltier element when a target temperature of at least one receptacle is reached in such a way that the temperature of at least one receptacle remains substantially constant. In this respect, the Peltier element can be alternately supplied with or without electrical voltage so that current flows temporarily through the Peltier element. For example, the control unit switches a circuit in which the Peltier element and a power source are integrated on or off depending on the detected temperature compared to the target temperature.

According to a further development of the temperature control device, the control unit is further configured to take into account an ambient temperature measured by an ambient temperature sensor in the controlled heating or cooling power in such a way that the heating or cooling power is increased, reduced or prevented in predetermined temperature ranges of the ambient temperature. For example, in an environment whose temperature is higher than the target temperature, further heating of the eye pad or philtrum pad can be prevented. Optionally, in an environment with an ambient temperature below a usual room temperature, the heating power can be increased to compensate for the heat lost from the eye pads or philtrum pads to the environment.

According to a further development of the temperature control device, if the temperature control device comprises at least two Peltier elements which are in operation simultaneously, the control unit is further configured to supply the heating or cooling power of the at least two Peltier elements jointly in phases to one of the at least one receptacle. In a temperature control device comprising two Peltier elements, one of the two Peltier elements can be configured to heat the eye pads and one of the two Peltier elements can be configured to cool the eye pads or philtrum pads. This means that the two Peltier elements can be operated independently of each other if, for example, only the eye pads or philtrum pads need to be cooled. In this case, the waste heat generated is dissipated to a housing and/or the environment. If heating of other eye pads or philtrum pads is also desired in parallel to cooling the eye pads or philtrum pads, the two Peltier elements can be thermally coupled in such a way that both contribute to heating or cooling the respective eye pads or philtrum pads.

According to a third aspect of the invention, a pad kit comprises at least one, preferably at least two eye pads, and/or a philtrum pad, and a temperature control device. The temperature control device comprises a Peltier element and at least one receptacle per pad. Each of the receptacles is also thermally coupled to a warm side or a cold side of the Peltier element. The temperature control device and the coupled receptacles make it possible to heat or cool one or more face pads according to the invention.

The receptacles may in some embodiments each comprise a protrusion for placing the face pad on the protrusion. This ensures secure fastening of the eye pads or philtrum pads to the protrusions.

According to an alternative embodiment, the receptacles are configured as recesses substantially adapted to the shape of the face pads. This has the advantage of providing a large contact surface between the receptacles and the face pads, which improves heat transfer between the receptacles and the eye pads.

According to one embodiment, the pad kit comprises two eye pads according to the invention and two receptacles, one of the receptacles being thermally coupled to the warm side and one of the receptacles being thermally coupled to the cold side of the Peltier element. This allows a warm and a cold eye pad to be used alternately and immediately one after the other. This causes an increased temperature difference between the user's skin and the second eye pad used. A large temperature difference on the user's skin can achieve a beneficial cosmetic improvement in the appearance of the skin.

According to the preferred embodiment of the pad kit according to the invention, the kit comprises four eye pads and four receptacles, two of the receptacles being thermally coupled to the warm side and two of the receptacles being thermally coupled to the cold side of the Peltier element. This enables treatment of both of the user's eyes simultaneously.

The eye pads may in some embodiments each comprise at least one magnet for magnetic fastening of the eye pads to the receptacles. This fixes the eye pads onto the receptacles.

According to various embodiments of the pad kit according to the invention, the temperature control device comprises at least one cover spanning at least one of the receptacles. As a result, the face pads are protected against mechanical damage. This cover may also include a hinge, which makes it easy to open and close the cover.

The receptacles may also be made of a temperature conducting material. This improves the heat transfer from the Peltier element to the face pads.

According to some embodiments of the pad kit according to the invention, each of the receptacles comprises a temperature sensor, and the temperature control device comprises a control unit connected to the temperature sensors and the Peltier element, which is configured to regulate a heating or cooling power of the Peltier element on the basis of a temperature of the receptacles detected by the temperature sensors. This prevents the face pads from being heated to a temperature or cooled to a temperature that would supply burn or frostbite symptoms when applied to a user's skin.

In some embodiments, the control unit is configured to regulate the heating or cooling power of the Peltier element when a target temperature of the receptacles is reached so that the temperature of the receptacles is kept substantially constant. This keeps the face pads at a constant temperature that is optimal for an application when they are connected to the temperature control device via the receptacles.

BRIEF DESCRIPTION OF THE DRAWINGS

Preferred and alternative embodiments of the eye pad according to the invention and the pad kit according to the invention are explained in more detail below on the basis of the figures.

FIG. 2a to FIG. 8b show different embodiments of the face pads according to the invention in a cross-sectional view.

DETAILED DESCRIPTION OF SOME EMBODIMENTS

Figure 1:
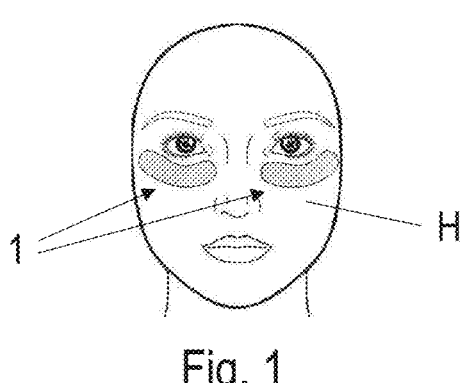
FIG. 1 shows two face pads according to the invention during application.

FIG. 1 shows two face pads 1 according to the invention, which have been placed on a user's skin H under the eyes. The face pads can thus be referred to as eye pads 1 and are used for cosmetic treatment of the area under the user's eyes covered by the eye pads 1.

In the course of such an exemplary treatment, the eye pads 1 according to the invention are first heated to a first target temperature, such as 40° C., then applied to the user's skin H under the eyes or in the periocular area, and fastened by means of a suction force. After the skin H has been warmed by the eye pads 1 they are removed again and a cream, preferably an eye cream such as an anti-wrinkle cream, is applied to the periocular area of the user's eyes in the area warmed by the eye pads. Subsequently, the same or additional eye pads that have been cooled to a second target temperature, such as 5° C., are applied to these areas and fastened again using suction force. The heating effect favors the receptacle of the cream by the skin H, wherein the subsequent cooling helps to close the pores of the skin H again. This improves the effect of the applied skin cream.

Figures 2A, 2B:
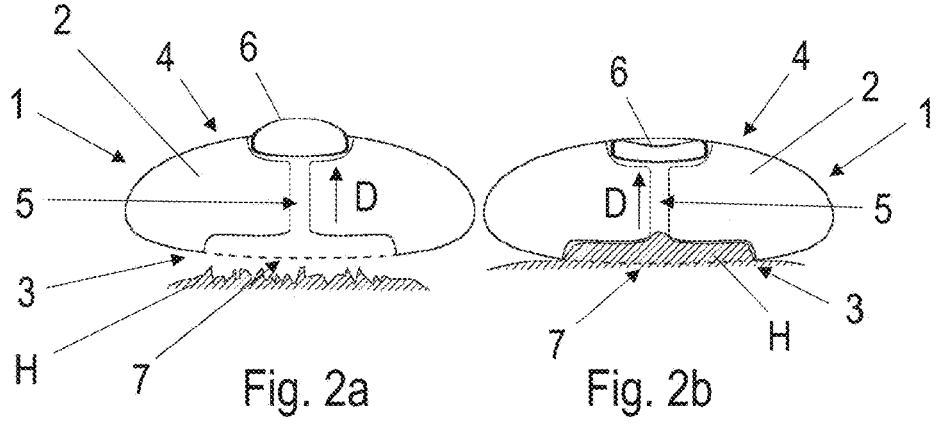

A sectional view of an eye pad 1 according to the invention is shown in FIG. 2a. The eye pad 1 according to the invention comprises an eye pad body 2, a first side 3 for resting on the user's skin H, and a second side 4 substantially opposite the first side 3. The eye pad body 2 comprises a passage 5 from the first side 3 to the second side 4. The eye pad 1 also comprises a negative pressure generating element 6 which is disposed on the second side 4 at one end of the passage 5 and preferably extends at least partially into the passage 5. The negative pressure generating element 6 is at least partially elastic and can, for example, be designed as a hollow body with an at least partially elastic shell comprising a hole oriented in the direction of the passage 5. The negative pressure generating element 6 is configured to provide a suction force in the passage 5 through the eye pad body 2 as a result of an elastic deformation of the negative pressure generating element 6 when the first side 3 of the eye pad body 2 is placed on the skin H of the user. When attaching the eye pad 1 according to the invention, the first side 2 is thus placed on the user's skin H, and subsequently or simultaneously a force is exerted on the negative pressure generating element 6. This reversibly deforms the negative pressure generating element 6. Due to the reversible deformation, if the negative pressure generating element 6 is configured as an at least partially elastic hollow body as described above, a volume of the negative pressure generating element 6 is reduced. As the passage 5 on the first side 3 is blocked by the user's skin H, a suction effect is created in the passage 5. As a result, the eye pad 1 is sucked onto the user's skin H and reversibly fastened to it. This state is shown in FIG. 2*b*. In FIG. 2*a* to FIG. 8*b*, in the figures marked with the letter b, the respective embodiment of the eye pad 1 according to the invention is always shown in the state in which it is suctioned onto the user's skin H, i.e. in the attached state.

As can be seen in FIGS. 2*a* to 8*b*, the passage 5 preferably comprises a larger opening 7 on the first side 3 than on the second side 4. This increases the area on the user's skin H to which the suction force is distributed. This reduces the likelihood of the suction effect damaging vessels in the user's skin H. In addition, this further improves the wearing comfort of the eye pad 1 according to the invention.

Figures 3A, 3B:
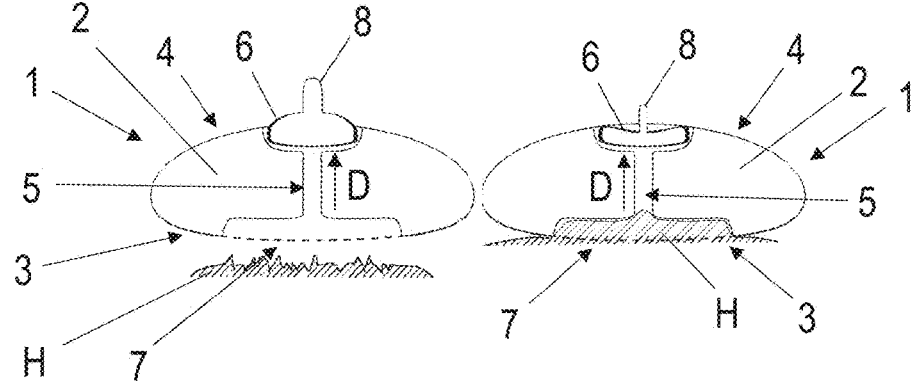

FIG. 3*a* shows the eye pad 1 according to the invention in an alternative embodiment. According to this embodiment, the negative pressure generating element 6 comprises an extension 8 protruding from the second side 3. This makes it easier for the user of the eye pad 1 according to the invention to grip the negative pressure generating element 6 and deform it.

Figures 4A, 4B:
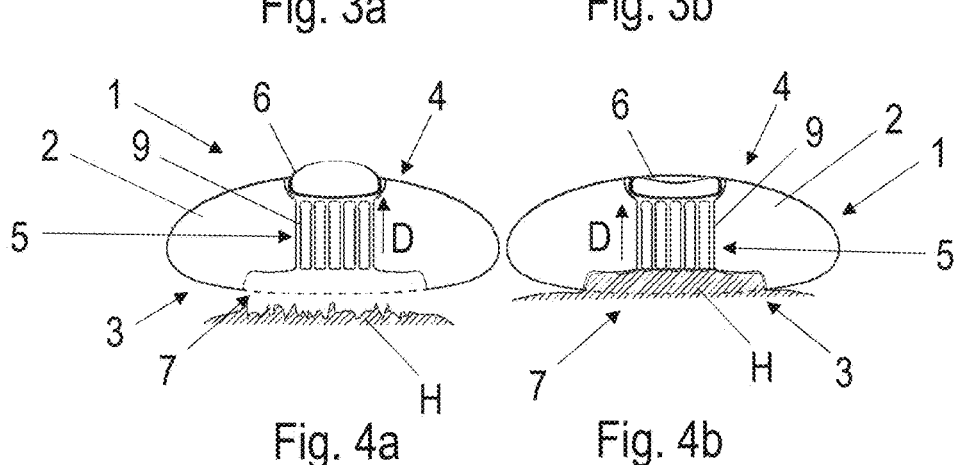

According to the preferred embodiment shown in FIG. 4*a* and FIG. 4*b*, the passage 5 comprises a plurality of slots and/or holes 9 oriented substantially in a passage direction D. This divides the passage 5 into several sections, whereby the suction effect is distributed over the several slots and/or holes 9. This distributes the force generated by the suction effect over a larger area of the surface of the skin H.

Figures 5A, 5B, 6A, 6B, 7A, 7B, 8A, 8B:
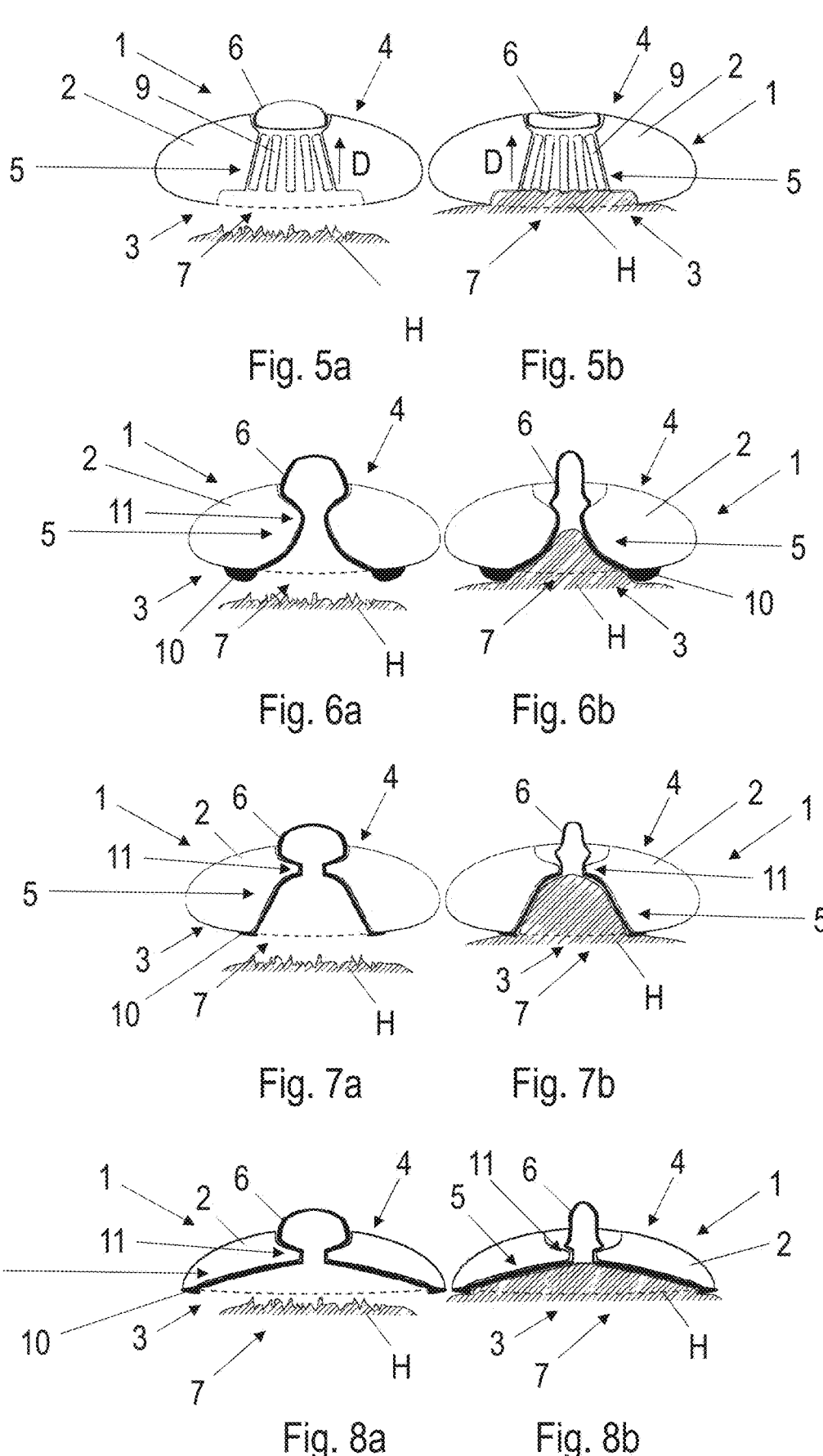

According to an embodiment variant of the preferred embodiment of the eye pad 1 according to the invention, as shown in FIG. 5*a* and FIG. 5*b*, the slots and/or holes 9 are disposed at an acute angle to one another, narrowing in the direction of the second side 4. This further increases the area of the user's skin H that is exposed to the suction effect.

FIG. 6*a* to FIG. 8*b* show embodiments of the eye pad 1 according to the invention, in which the negative pressure generating element 6 extends from the second side 4 to the first side 3 through the passage 5. The negative pressure generating element 6 is designed as an at least partially elastic insert in the eye pad body 2 that is open on one side in the direction of the first side 3. By designing the negative pressure generating element 6 as an insert in the eye pad body 2 that is open on one side, the advantage is achieved that a better seal is achieved between the negative pressure generating element 6 and the eye pad body 2, as well as the skin H of the user. Preferably, as shown in FIG. 6*a* and FIG. 6*b*, the negative pressure generating element 6 comprises a flexible lip 10 arranged on the first side 3 of the eye pad body 2 and surrounding the passage 5. The flexible lip 10 further improves the seal against the user's skin H, allowing the eye pad 1 to adhere better to the user's skin H.

As can be seen in FIG. 6*a* to FIG. 8*b*, the passage 5 may comprise a narrow point 11 between the first side 3 and the second side 4. As a result, the extent to which the user's skin H can be sucked into the eye pad body 2 is limited.

According to the preferred embodiment of the eye pad 1 according to the invention, the eye pad body 2 is made of a metal, and preferably covered with a soft material such as silicone, latex and/or rubber. This results in an increased heat capacity of the eye pad body 2, whereby the warming or cooling effect on the user's skin H can be maintained over a longer period of time when the eye pad is heated or cooled. Alternatively, or additionally, the interior of the eye pad body 2 may thus comprise a temperature in the range of 55° C. to 65° C., while the outer surface of the eye pad 1, with or without coating, would comprise a temperature in the range of 35° C. to 45° C. Covering the eye pad body 2 with silicone, latex and/or rubber provides a soft surface that is pleasant to the touch and also thermally insulates the eye pad body 2. As a result, the risk of burns or frostbite occurring on the user's skin H when using the eye pad 1 is reduced.

Figure 9:
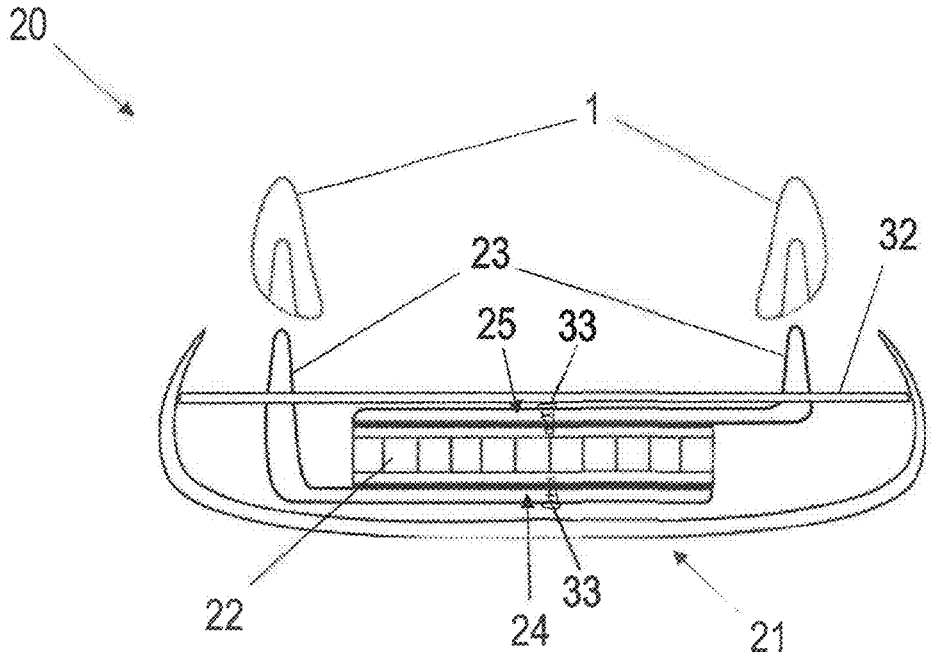
FIG. 9 shows a pad kit according to the invention with two eye pads and a temperature control device.

FIG. 9 shows a schematic representation of a pad kit 20 according to the invention, which comprises two face pads 1 according to the invention. These face pads 1 are shown in FIG. 9 as eye pads 1, but it should be clear that the face pads 1 can also comprise other support elements such as pads that can be applied in the cutaneous area between the nose, upper lip and nasolabial folds ("philtrum pads"). In the following description of embodiments, reference is made to eye pads—however, analogous technical considerations apply equally to other face pads 1 such as philtrum pads in particular.

The kit 20 further comprises a temperature control device 21, which comprises a Peltier element 22 and at least one receptacle 23 per eye pad 1. Each of the receptacles 23 is thermally coupled to a warm side 24 or a cold side 25 of the Peltier element 22. This provides a means of heating or cooling the eye pads 1 before they are applied to the user's skin H. In addition, the temperature control device 21 comprises a fixing device that is thermally decoupled from the Peltier element 22. The fixing device 33 fastens the receptacle 23 to the warm side 25 or the cold side 24 by means of a screw connection. In this respect, a portion of the receptacle 23 is clamped between the fixing device 33 and the warm side 25 or the cold side 24. As shown in FIG. 9, the receptacles 23 preferably each comprise a protrusion for receiving the eye pad 1 and placing it on the protrusion. This ensures a secure coupling of the eye pad 1 with the receptacle 23. In addition, this increases the contact surface between the eye pad 1 and the receptacle 23, allowing the eye pad 1 to be heated or cooled as quickly as possible. According to one embodiment of the kit 20 according to the invention, the kit 20 comprises two eye pads 1 and two receptacles 23, wherein one of the receptacles 23 is thermally coupled to the cold side 25 and one of the receptacles 23 is thermally coupled to the warm side 24 of the Peltier element 22. According to the preferred embodiment, the kit 20 comprises four eye pads 1 and four receptacles 23, two of the receptacles 23 being thermally coupled to the warm side 24 and two of the receptacles 23 being thermally coupled to the cold side 25 of the Peltier element 22.

Figure 10:
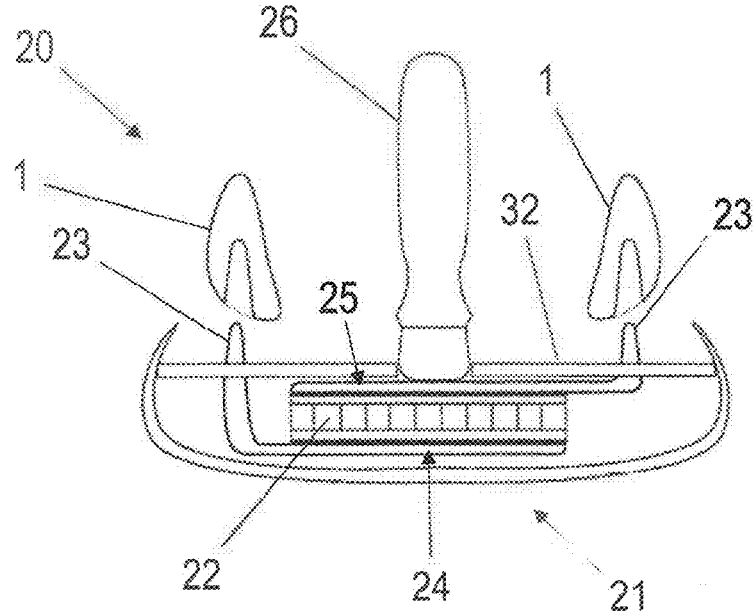
FIG. 10 shows the pad kit according to the invention as shown in FIG. 9 with an additional eye roller.

The cold side 25 of the Peltier element 25 can also be used, for example, to cool an eye roller 26 or the like as part of the kit 20 according to the invention, as shown in FIG. 10. Additionally, or alternatively, the temperature control device 21 may also comprise a mounting means for the eye roller 26 and/or a cream can 27 as shown in FIG. 11, wherein the eye roller 26 and/or the cream can 27 are thermally coupled to the cold side 25 or the warm side 24 of the Peltier element 22 in a state received on the temperature control device 21.

This has the advantage that the eye roller 26 and/or the cream jar 27 can be heated or cooled at the same time as the eye pads 1.

Optionally, the eye pad 1 may comprise a first and a second area that are thermally decoupled from each other, for example by a thermally insulating adhesive. This means that the first and second areas can be cooled or heated independently of each other. In this respect, for example, the first area of the eye pad 1 is thermally coupled to the cold side 25 and the second area to the warm side 24. In this variant, the eye pad 1 is supported in particular by two receptacles 23, with one receptacle cooling the first area, for example, while the other receptacle heats the second area. The two receptacles 23 can optionally be disposed on opposite sides of the eye pad 1 or on the same side.

Figures 11, 12, 13:
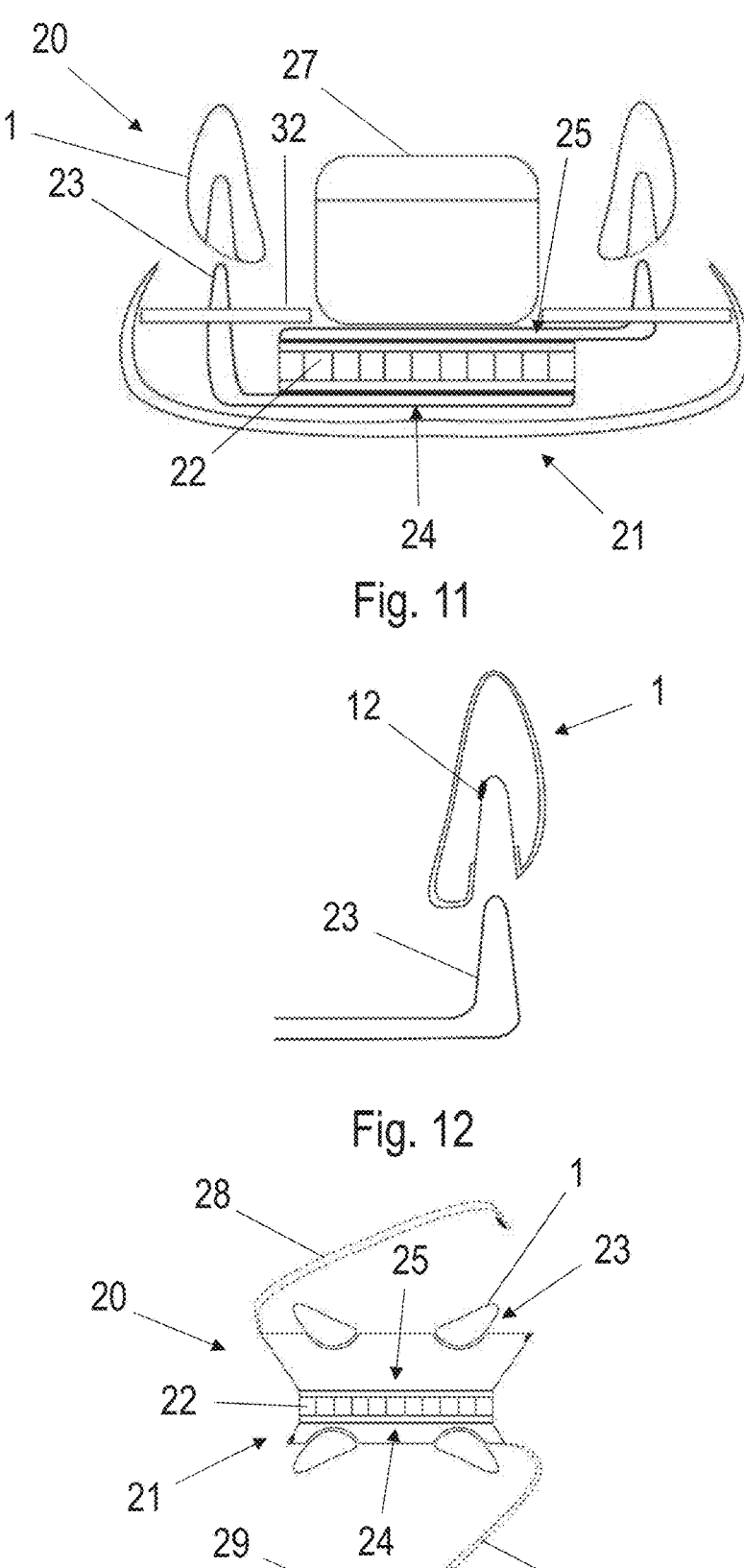
FIG. 11 shows the pad kit according to the invention as shown in FIG. 9 with an additional cream container.
FIG. 12 shows a cross-sectional view through a receptacle of the temperature control device and an eye pad with a magnet.
FIG. 13 shows an alternative embodiment of the pad kit according to the invention with additional covers.

As can be seen in FIG. 12, the eye pads 1 according to their preferred embodiment can each comprise at least one magnet 12 for magnetically fastening the eye pads 1 to the receptacles 23. This provides a secure fastening of the eye pads 1 to the receptacles 23.

According to an alternative embodiment of the kit 20 according to the invention, the receptacles 23, as can be seen in FIG. 13, are configured as depressions substantially adapted to the shape of the eye pads 1. In addition, it can be seen in FIG. 13 that the kit 20 comprises four eye pads 1, two of the receptacles 23 being thermally coupled to the warm side 24 and two of the receptacles 23 being thermally coupled to the cold side 25 of the Peltier element 22. In addition, the temperature control device 21 preferably comprises at least one cover 28 spanning at least one of the receptacles 23. In FIG. 13, the temperature control device 21 is shown with two covers 28, one of the covers 28 spanning two receptacles 23 in each case. In addition, the covers 28 preferably each comprise or include a hinge, which is not evident in the Figures. This provides a swivel connection of the cover 28 with the temperature control device 21. In addition, the cover 28 may include a magnet 29 for reversibly closing the cover 28. In all embodiments of the kit 20 according to the invention, the receptacles 23 are preferably made of a temperature conducting material, whereby the temperature transfer from the Peltier element 22 to the eye pads 1 is improved.

Figure 14:
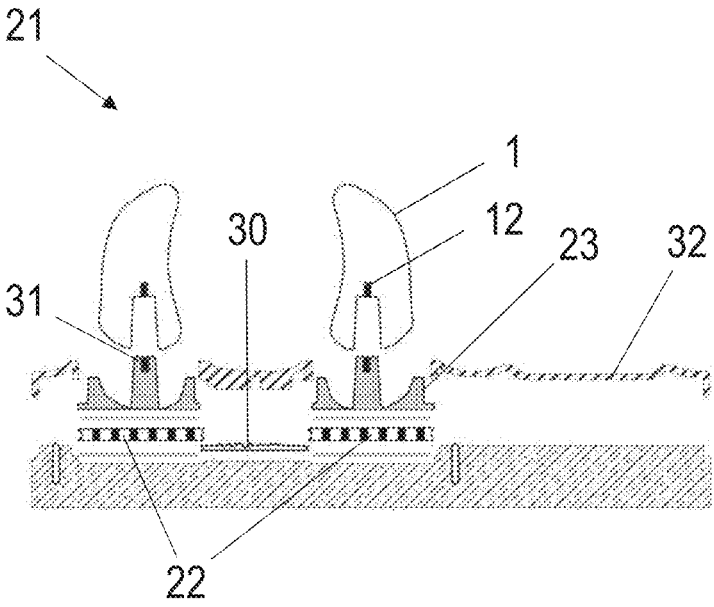
FIG. 14 shows a temperature control device of the pad kit according to the invention in an alternative embodiment with two Peltier elements.

FIG. 14 shows a section of a temperature control device 21 of an alternative embodiment of the eye pad kit 20 according to the invention. In the temperature control device 21 shown in FIG. 14, two Peltier elements 22 are provided, each of which is thermally coupled to a receptacle 23. In addition, a control unit 30 for controlling the respective Peltier elements 22 is shown in FIG. 14. This control unit 30 can also be provided in embodiments of the temperature control device 21 with only one Peltier element 22. Depending on the orientation or activation of the Peltier elements 22 by the control unit 30, the receptacles are thus coupled to the warm side 24 or the cold side 25 of the respective Peltier element 22. Preferably, each of the receptacles 23 also comprises a temperature sensor 31, which can also be seen in FIG. 14. The control unit 30 is connected to the temperature sensors 31 and the Peltier element 22. The control unit 30 regulates the heating or cooling power of the Peltier element 22 or the Peltier elements 22 on the basis of the temperature of the receptacles 23 detected by the temperature sensors 31. In addition, when a target temperature of the receptacles 23 is reached, the control unit 30 can regulate the heating or cooling power of the Peltier element 22 in such a way that the temperature of the receptacles 23 is kept substantially constant. For example, it is also possible to significantly increase the heating power of the Peltier elements 22 in a "boost" mode for a certain period of time, for example at the beginning of a heating process, in order to shorten the waiting time until the target temperature is reached in the eye pads 1 or the receptacles 23. FIG. 14 also shows a section through a protective layer 32, which, among other things, covers the control unit 30 and protects it from mechanical damage or prevents water from entering the temperature control device 21. This protective layer 32 can also be provided in all embodiments of the kit 20 according to the invention.

Further, the control unit 30 is configured to take into account an ambient temperature measured by an ambient temperature sensor in the controlled heating or cooling power. The control unit 30 increases, reduces or stops the heating or cooling power in predetermined temperature ranges of the ambient temperature. For example, in an environment where the temperature is higher than 55° C., for example, further heating of the eye pad can be prevented, as in this case a malfunction or incorrect operation can be assumed. Alternatively, or additionally, the control unit 30 is further configured to supply the heating or cooling power of the two Peltier elements 22 jointly in phases to one of the two receptacles 23 if the user wishes to simultaneously cool the receptacle coupled to the cold side as well as heat the receptacle coupled to the warm side and activates this in each case. However, the present invention is not limited to the embodiment according to FIG. 14 with two Peltier elements, but can also comprise only some of the features described. Thus, a temperature control device 21 with two Peltier elements 22 can, for example, also put them into operation independently of each other.

The control unit 30 preferably also comprises a communication interface, which is configured to produce a data connection with a computer unit. The computer unit can, for example, be configured as a smartphone, server or tablet computer, whereby the control unit 30 is configured to regulate the power of the Peltier element 22 on the basis of data received from the computer unit via the communication interface.

In alternative embodiments, the temperature control device 21 may further comprise, for example, an illumination device which illuminates the eye pads 1 in particular with UV light. The illumination device can optionally be disposed in the cover, on the housing or in another manner such that a large part of the eye pad 1, in particular the skin contact surface, is illuminated by the illumination device. In this way, the number of bacteria/viruses/germs that are present, for example, on the surface of the eye pads 1 can be reduced.

What is claimed is:

1. A temperature control device for face pads, comprising:
   a Peltier element;
   at least one receptacle for supporting a face pad, wherein each of the at least one receptacle is thermally coupled to a warm side or a cold side of the Peltier element; and
   a fixing device, which is thermally decoupled from the Peltier element and which fastens the at least one receptacle on the warm side or the cold side in at least one of a form-fitting manner and a force-locking manner;
   wherein the at least one receptacle comprises at least one magnet for magnetically fastening a face pad to the receptacle, and
   wherein the at least one receptacle comprises a protrusion for placing a face pad on the protrusion and wherein the protrusion of the at least one receptacle comprises the at least one magnet for magnetically fastening a face pad to the receptacle.

2. The temperature control device of claim 1, wherein the at least one receptacle is shaped so as to correspond substantially in portions to a shape of the face pad.

3. The temperature control device of claim 1, comprising two receptacles, wherein one of the receptacles is thermally coupled to the warm side and one of the receptacles is thermally coupled to the cold side of the Peltier element, and wherein in each case two face pads can be supported by the two receptacles.

4. The temperature control device of claim 1, wherein the at least one receptacle comprises a temperature conducting material.

5. The temperature control device of claim 4, wherein the at least one receptacle comprises at least one of aluminum, copper, an aluminum alloy, and a copper alloy.

6. The temperature control device of claim 5, wherein the at least one receptacle is produced by a die casting method or a forging method.

7. The temperature control device of claim 1, wherein the at least one receptacle comprises a temperature sensor and a control unit connected to the temperature sensor and the Peltier element, which is configured to regulate a heating or cooling power of the Peltier element on the basis of a temperature of the at least one receptacle detected by the temperature sensor.

8. The temperature control device of claim 7, wherein the control unit is configured to regulate the heating or cooling power of the Peltier element when a target temperature of the at least one receptacle is reached such that the temperature of the at least one receptacle remains substantially constant.

9. The temperature control device of claim 7, wherein the control unit is further configured to take into account an ambient temperature measured by an ambient temperature sensor in the controlled heating or cooling power in such a way that the heating or cooling power is increased, reduced or prevented in predetermined temperature ranges of the ambient temperature.

10. The temperature control device of claim 7, wherein, the temperature control device comprises at least two Peltier elements which are in operation simultaneously, and wherein the control unit is further configured to supply the heating or cooling power of the at least two Peltier elements jointly in phases to one of the at least one receptacle.

11. A temperature control device for face pads, comprising:

a Peltier element;

at least one receptacle for supporting a face pad, wherein each of the at least one receptacle is thermally coupled to a warm side or a cold side of the Peltier element; and a fixing device, which is thermally decoupled from the Peltier element and which fastens the at least one receptacle on the warm side or the cold side in at least one of a form-fitting manner and a force-locking manner;

wherein the at least one receptacle includes two receptacles, wherein one of the receptacles is thermally coupled to the warm side of the Peltier element and one of the receptacles is thermally coupled to the cold side of the Peltier element, and wherein in each case two face pads can be supported by the two receptacles.

* * * * *